(12) United States Patent
Kayser et al.

(10) Patent No.: US 6,346,637 B1
(45) Date of Patent: Feb. 12, 2002

(54) ETHER CONTAINING SILOXY COMPOUNDS

(75) Inventors: Francois Kayser, Luxembourg; Wolfgang Lauer, Mersch, both of (LU); Thierry Florent Edme Materne, Viville (BE)

(73) Assignee: The Goodyear Tire & Rubber Company, Akron, OH (US)

( * ) Notice: Subject to any disclaimer, the term of this patent is extended or adjusted under 35 U.S.C. 154(b) by 0 days.

(21) Appl. No.: 09/613,745

(22) Filed: Jul. 11, 2000

Related U.S. Application Data
(60) Provisional application No. 60/148,174, filed on Aug. 10, 1999.

(51) Int. Cl.$^7$ .................................................. C07F 7/08
(52) U.S. Cl. ...................... 556/444; 525/342; 525/343; 525/350; 152/208; 152/209.1
(58) Field of Search ................. 536/444; 525/342, 525/343, 350; 152/208, 209.1

(56) References Cited

U.S. PATENT DOCUMENTS

| | | | | |
|---|---|---|---|---|
| 3,218,344 A | * | 11/1965 | Bailey | 556/444 |
| 3,338,870 A | * | 8/1967 | Nitzsche et al. | 556/444 |
| 3,410,820 A | * | 11/1968 | Harrod | 556/444 |
| 4,379,891 A | | 4/1983 | Haynes | 525/342 |
| 4,775,415 A | | 10/1988 | Mohr | 106/14.05 |

FOREIGN PATENT DOCUMENTS

DE  2159723  6/1973

OTHER PUBLICATIONS

"New Silane Coupling Agents from Renewable Resources for Rubber Reinforcement" by N. D. Ghatge and R. S. Khisti as published by *Elastomerics*, Jan. 1985, vol. 117, No. 1, pp. 23–26, XP002106806.

* cited by examiner

*Primary Examiner*—Paul F. Shaver
(74) *Attorney, Agent, or Firm*—Bruce J. Hendricks

(57) ABSTRACT

The present invention relates to compounds of the formula

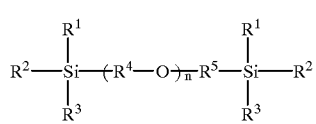

I where $R^1$, $R^2$ and $R^3$ are independently selected from alkoxy radicals having from 1 to 8 carbon atoms; $R^4$ and $R^5$ are independently selected from the group consisting of alkylene having 1 to 12 carbons, arylenes having 6 carbon atoms and alkarylenes having 7 to 10 carbon atoms and n is an integer of from 1 to 10. These compounds may be used in rubber compositions.

18 Claims, No Drawings

ETHER CONTAINING SILOXY COMPOUNDS

This Appln claims benefit of Prov. No. 60/148,174 filed Aug. 10, 1999.

FIELD OF THE INVENTION

The present invention relates to ether containing siloxy compounds which may be used as silica couplers in rubber. The present invention also relates to a silica-filled rubber composition containing ether containing siloxy compounds and the processing of a sulfur-curable rubber composition containing silica and ether containing siloxy compounds.

BACKGROUND OF THE INVENTION

Sulfur containing organosilicon compounds are useful as reactive coupling agents between rubber and silica fillers providing for improved physical properties. They are also useful as adhesion primers for glass, metals and other substrates.

U.S. Pat. Nos. 3,842,111, 3,873,489 and 3,978,103 disclose the preparation of various sulfur containing organosilicon compounds. These organosilicon compounds are prepared by reacting (a) 2 moles of a compound of the formula:

Z—Alk—hal where hal is a chlorine, bromine or iodine; Z is:

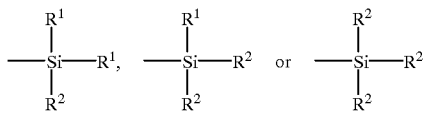

where $R^1$ is an alkyl of 1 to 4 carbon atoms or phenyl and $R^2$ is alkoxy of 1 to 8 carbon atoms; or cycloalkoxy of 5 to 8 carbon atoms; or alkylmercapto with 1 to 8 carbon atoms; Alk is a divalent aliphatic hydrocarbon or unsaturated hydrocarbon or a cyclic hydrocarbon containing 1 to 18 carbon atoms; with (b) 1 mole of a compound of the formula:

Me$_2$S$_n$ where Me is ammonium or a metal atom and n is a whole number from 2 to 6.

SUMMARY OF THE INVENTION

The present invention relates to ether containing siloxy compounds and their use in silica-filled rubber.

DETAILED DESCRIPTION OF THE INVENTION

There is disclosed a compound of the formula:

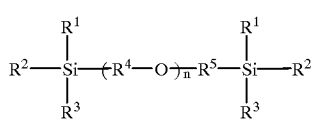

I where $R^1$, $R^2$ and $R^3$ are independently selected from alkoxy radicals having from 1 to 8 carbon atoms; $R^4$ and $R^5$ are independently selected from the group consisting of alkylenes having 1 to 12 carbon atoms, arylenes having 6 carbon atoms and alkarylenes having 7 to 10 carbon atoms and n is an integer of from 1 to 10.

There is also disclosed a method for processing a rubber composition which comprises mixing (i) 100 parts by weight of at least one sulfur vulcanizable elastomer selected from conjugated diene homopolymers and copolymers and from copolymers of at least one conjugated diene and aromatic vinyl compound; with (ii) 0.05 to 10 phr of a compound of the formula:

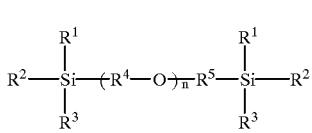

I where $R^1$, $R^2$ and $R^3$ are independently selected from alkoxy radicals having from 1 to 8 carbon atoms; $R^4$ and $R^5$ are independently selected from the group consisting of alkylenes having 1 to 12 carbon atoms, arylenes having 6 carbon atoms and alkarylenes having 7 to 10 carbon atoms and n is an integer of from 1 to 10.

There is also disclosed a sulfur-vulcanizable rubber composition comprising an elastomer containing olefinic unsaturation and a compound of the formula:

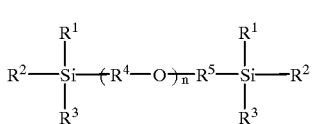

I where $R^1$, $R^2$ and $R^3$ are independently selected from alkoxy radicals having from 1 to 8 carbon atoms; $R^4$ and $R^5$ are independently selected from the group consisting of alkylenes having 1 to 12 carbon atoms, arylenes having 6 carbon atoms and alkarylenes having 7 to 10 carbon atoms and n is an integer of from 1 to 10.

The present invention may be used to process sulfur vulcanizable rubbers or elastomers containing olefinic unsaturation. The phrase "rubber or elastomer containing olefinic unsaturation" is intended to include both natural rubber and its various raw and reclaim forms as well as various synthetic rubbers. In the description of this invention, the terms "rubber" and "elastomer" may be used interchangeably, unless otherwise prescribed. The terms "rubber composition," "compounded rubber" and "rubber compound" are used interchangeably to refer to rubber which has been blended or mixed with various ingredients and materials and such terms are well known to those having skill in the rubber mixing or rubber compounding art. Representative synthetic polymers are the homopolymerization products of butadiene and its homologues and derivatives, for example, methylbutadiene, dimethylbutadiene and pentadiene as well as copolymers such as those formed from butadiene or its homologues or derivatives with other unsaturated monomers. Among the latter are acetylenes, for example, vinyl acetylene; olefins, for example, isobutylene, which copolymerizes with isoprene to form butyl rubber; vinyl compounds, for example, acrylic acid, acrylonitrile (which polymerize with butadiene to form NBR), methacrylic acid and styrene, the latter compound polymerizing with butadiene to form SBR, as well as vinyl esters and various unsaturated aldehydes, ketones and ethers, e.g., acrolein, methyl isopropenyl ketone and vinyl-ethyl ether. Specific examples of synthetic rubbers include neoprene (polychloroprene), polybutadiene (including cis-1,4-polybutadiene), polyisoprene (including cis-1,4-polyisoprene), butyl rubber, halobutyl rubber such as chlorobutyl rubber or bromobutyl rubber, styrene/isoprene/butadiene rubber, copolymers of 1,3-butadiene or isoprene with monomers such as styrene, acrylonitrile and methyl methacrylate, as well as ethylene/propylene terpolymers, also known as ethylene/propylene/diene monomer (EPDM), and in particular, ethylene/propylene/dicyclopentadiene terpolymers. Additional examples of rubbers which may be used include silicon-coupled and tin-coupled star-branched polymers. The preferred rubber or elastomers are polybutadiene and SBR.

In yet another aspect of the present invention, it is preferred to use a rubber or elastomer containing olefinic unsaturation and an additional functional group reactive with the siloxy compounds of Formula I of the present invention. Representative functional groups include halogens, such as Cl and Br; alkoxy groups, such as methoxy groups; and, pseudohalogens, such as —SCN.

In yet another aspect of the invention, the elastomer may be a siloxy-terminated styrene-butadiene copolymer, siloxy-terminated isoprene-butadiene copolymer and siloxy-terminated styrene-isoprene-butadiene terpolymer.

In one aspect the rubber is preferably of at least two of diene based rubbers. For example, a combination of two or more rubbers is preferred such as cis 1,4-polyisoprene rubber (natural or synthetic, although natural is preferred), 3,4-polyisoprene rubber, styrene/isoprene/butadiene rubber, emulsion and solution polymerization derived styrene/butadiene rubbers, cis 1,4-polybutadiene rubbers and emulsion polymerization prepared butadiene/acrylonitrile copolymers.

In one aspect of this invention, an emulsion polymerization derived styrene/butadiene (E-SBR) might be used having a relatively conventional styrene content of about 20 to about 28 percent bound styrene or, for some applications, an E-SBR having a medium to relatively high bound styrene content, namely, a bound styrene content of about 30 to about 45 percent.

The relatively high styrene content of about 30 to about 45 for the E-SBR can be considered beneficial for a purpose of enhancing traction, or skid resistance, of the tire tread. The presence of the E-SBR itself is considered beneficial for a purpose of enhancing processability of the uncured elastomer composition mixture, especially in comparison to a utilization of a solution polymerization prepared SBR (S-SBR).

By emulsion polymerization prepared E-SBR, it is meant that styrene and 1,3-butadiene are copolymerized as an aqueous emulsion. Such are well known to those skilled in such art. The bound styrene content can vary, for example, from about 5 to about 50 percent. In one aspect, the E-SBR may also contain acrylonitrile to form a terpolymer rubber, as E-SBAR, in amounts, for example, of about 2 to about 30 weight percent bound acrylonitrile in the terpolymer.

Emulsion polymerization prepared styrene/butadiene/acrylonitrile copolymer rubbers containing about 2 to about 40 weight percent bound acrylonitrile in the copolymer are also contemplated as diene based rubbers for use in this invention.

The solution polymerization prepared SBR (S-SBR) typically has a bound styrene content in a range of about 5 to about 50, preferably about 9 to about 36, percent. The S-SBR can be conveniently prepared, for example, by organo lithium catalyzation in the presence of an organic hydrocarbon solvent.

A purpose of using S-SBR is for improved tire rolling resistance as a result of lower hysteresis when it is used in a tire tread composition.

The 3,4-polyisoprene rubber (3,4-PI) is considered beneficial for a purpose of enhancing the tire's traction when it is used in a tire tread composition. The 3,4-PI and use thereof is more fully described in U.S. Pat. No. 5,087,668 which is incorporated herein by reference. The Tg refers to the glass transition temperature which can conveniently be determined by a differential scanning calorimeter at a heating rate of 10° C. per minute.

The cis 1,4-polybutadiene rubber (BR) is considered to be beneficial for a purpose of enhancing the tire tread's wear, or treadwear. Such BR can be prepared, for example, by organic solution polymerization of 1,3-butadiene. The BR may be conveniently characterized, for example, by having at least a 90 percent cis 1,4-content.

The cis 1,4-polyisoprene and cis 1,4-polyisoprene natural rubber are well known to those having skill in the rubber art.

The term "phr" as used herein, and according to conventional practice, refers to "parts by weight of a respective material per 100 parts by weight of rubber, or elastomer."

The ether containing siloxy compounds used in the present invention are of the formula:

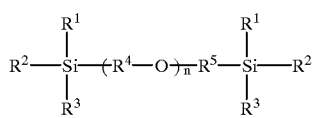

I where $R^1$, $R^2$ and $R^3$ are independently selected from alkoxy radicals having from 1 to 8 carbon atoms; $R^4$ and $R^5$ are independently selected from the group consisting of alkylenes having 1 to 12 carbon atoms, arylenes having 6 carbon atoms and alkarylenes having 7 to 10 carbon atoms and n is an integer of from 1 to 10. Preferably, each $R^1$, $R^2$ and $R^3$ are alkoxy radicals having from 1 to 3 carbon atoms; $R^4$ and $R^5$ are each an alkylene having from 1 to 5 carbon atoms and n is 1. The ether containing siloxy compounds of Formula I may comprise a high purity product or mixture of products of Formula I.

The compound of Formula I is added to the rubber in an amount ranging from 0.05 to 10 phr. Preferably, the amount ranges from 1 to 5 phr.

Representative of the ether containing compounds of Formula I include but are not limited to:

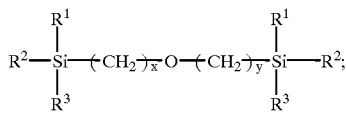

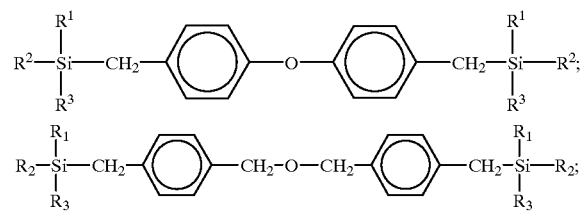

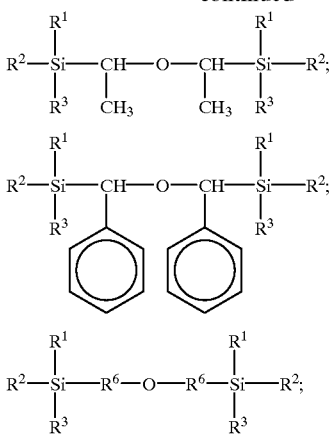

wherein x and y are individually selected from a group of integers of from 1 to 12 and $R^6$ is a cycloaliphatic group having from 5 to 8 carbon atoms in the ring. Preferably, x is from 1 to 5, y is from 1 to 5 and $R^6$ is a cycloaliphatic group having 5 carbon atoms in the ring.

The siloxy compound of Formula I may be prepared by the reaction scheme listed below:

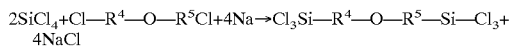

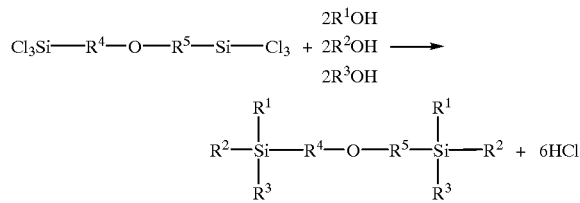

The reaction may be conducted in the presence of a suitable solvent. The primary criteria is to use a solvent which does not react with the starting materials or end product. Representative organic solvents include hexane, heptane, cyclohexane, xylene, benzene and toluene. Water is avoided to prevent reaction with the sodium and the siloxy groups of the compounds.

For ease in handling, the siloxy of Formula I may be used per se or may be deposited on suitable carriers. Examples of carriers which may be used in the present invention include silica, carbon black, alumina-silicates, alumina, clay, kieselguhr, cellulose, silica gel and calcium silicate.

The rubber composition should contain a sufficient amount of filler, if used, to contribute a reasonably high modulus and high resistance to tear. The filler may be added in amounts ranging from 10 to 150 phr. Representative fillers include silica, carbon black, aluminasilicates, clays, zeolites, modified starches, silica/carbon composites and the like. Preferably, silica is present in an amount ranging from 10 to 80 phr. If carbon black is also present, the amount of carbon black, if used, may vary. Generally speaking, the amount of carbon black will vary from 0 to 80 phr. Preferably, the amount of carbon black will range from 0 to 40 phr. It is to be appreciated that the silica coupler may be used in conjunction with a carbon black, namely pre-mixed with a carbon black prior to addition to the rubber composition, and such carbon black is to be included in the aforesaid amount of carbon black for the rubber composition formulation.

Where the rubber composition contains both silica and carbon black, the weight ratio of silica to carbon black may vary. For example, the weight ratio may be as low as 1:5 to a silica to carbon black weight ratio of 30:1. Preferably, the weight ratio of silica to carbon black ranges from 1:3 to 5:1. The combined weight of the silica and carbon black, as herein referenced, may be as low as about 30 phr, but is preferably from about 45 to about 90 phr.

The commonly employed siliceous pigments used in rubber compounding applications can be used as the silica in this invention, including pyrogenic and precipitated siliceous pigments (silica), although precipitate silicas are preferred. The siliceous pigments preferably employed in this invention are precipitated silicas such as, for example, those obtained by the acidification of a soluble silicate, e.g., sodium silicate.

Such silicas might be characterized, for example, by having a BET surface area, as measured using nitrogen gas, preferably in the range of about 40 to about 600, and more usually in a range of about 50 to about 300 square meters per gram. The BET method of measuring surface area is described in the *Journal of the American Chemical Society*, Volume 60, page 304 (1930).

The silica may also be typically characterized by having a dibutylphthalate (DBP) absorption value in a range of about 100 to about 400, and more usually about 150 to about 300.

The silica might be expected to have an average ultimate particle size, for example, in the range of 0.01 to 0.05 micron as determined by the electron microscope, although the silica particles may be even smaller, or possibly larger, in size.

Various commercially available silicas may be considered for use in this invention such as, only for example herein, and without limitation, silicas commercially available from PPG Industries under the Hi-Sil trademark with designations 210, 243, etc; silicas available from Rhone-Poulenc, with, for example, designations of Z1165MP and Z165GR and silicas available from Degussa AG with, for example, designations VN2 and VN3, etc.

The siloxy compounds of Formula I may be used alone and/or in combination with a symmetrical sulfur containing organosilicon compound. Examples of suitable sulfur containing organosilicon compounds are of the formula:

$$Z-Alk-S_n-Alk-Z \quad (II)$$

in which Z is selected from the group consisting of:

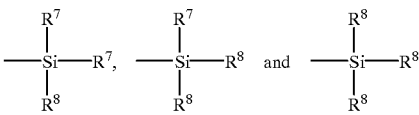

where $R^7$ is an alkyl group of 1 to 4 carbon atoms, cyclohexyl or phenyl;

$R^8$ is alkoxy of 1 to 8 carbon atoms, or cycloalkoxy of 5 to 8 carbon atoms;

Alk is a divalent hydrocarbon of 1 to 18 carbon atoms and n is an integer of 2 to 8.

Specific examples of sulfur containing organosilicon compounds which may be used in accordance with the present invention include: 3,3'-bis(triethoxysilylpropyl) disulfide, 3,3'-bis(triethoxysilylpropyl) tetrasulfide, 3,3'-bis(triethoxysilylpropyl) octasulfide, 3,3'-bis(trimethoxysilylpropyl) tetrasulfide, 2,2'-bis(triethoxysilylethyl) tetrasulfide, 3,3'-bis(trimethoxysilylpropyl) trisulfide, 3,3'-bis(triethoxysilylpropyl) trisulfide, 3,3'-bis (tributoxysilylpropyl) disulfide, 3,3'-bis (trimethoxysilylpropyl) hexasulfide, 3,3'-bis (trimethoxysilylpropyl) octasulfide, 3,3'-bis (trioctoxysilylpropyl) tetrasulfide, 3,3'-bis (trihexoxysilylpropyl) disulfide, 3,3'-bis(tri-2"-ethylhexoxysilylpropyl) trisulfide, 3,3'-bis (triisooctoxysilylpropyl) tetrasulfide, 3,3'-bis(tri-t-butoxysilylpropyl) disulfide, 2,2'-bis(methoxy diethoxy silyl ethyl) tetrasulfide, 2,2'-bis(tripropoxysilylethyl) pentasulfide, 3,3'-bis(tricyclonexoxysilylpropyl) tetrasulfide, 3,3'-bis(tricyclopentoxysilylpropyl) trisulfide, 2,2'-bis(tri-2"-methylcyclohexoxysilylethyl) tetrasulfide, -bis(trimethoxysilylmethyl) tetrasulfide, 3-methoxy ethoxy propoxysilyl 3'-diethoxybutoxysilylpropyltetrasulfide, 2,2'-bis(dimethyl methoxysilylethyl) disulfide, 2,2'-bis(dimethyl sec.butoxysilylethyl) trisulfide, 3,3'-bis(methyl-butylethoxysilylpropyl) tetrasulfide, 3,3'-bis(di t-butylmethoxysilylpropyl) tetrasulfide, 2,2'-bis(phenyl methyl methoxysilylethyl) trisulfide, 3,3,'-bis(diphenyl isopropoxysilylpropyl) tetrasulfide, 3,3'-bis(diphenyl cyclohexoxysilylpropyl) disulfide, 3,3'-bis(dimethyl ethylmercaptosilylpropyl) tetrasulfide, 2,2'-bis(methyl dimethoxysilylethyl) trisulfide, 2,2'-bis(methyl ethoxypropoxysilylethyl) tetrasulfide, 3,3'-bis(diethyl methoxysilylpropyl) tetrasulfide, 3,3'-bis(ethyl di-sec.butoxysilylpropyl) disulfide, 3,3'-bis(propyl diethoxysilylpropyl) disulfide, 3,3'-bis(butyl dimethoxysilylpropyl) trisulfide, 3,3'-bis(phenyl dimethoxysilylpropyl) tetrasulfide, 3-phenyl ethoxybutoxysilyl 3'-trimethoxysilylpropyl tetrasulfide, 4,4'-bis (trimethoxysilylbutyl) tetrasulfide, 6,6'-bis (triethoxysilylhexyl) tetrasulfide, 12,12'-bis (triisopropoxysilyl dodecyl) disulfide, 18,18'-bis (trimethoxysilyloctadecyl) tetrasulfide, 18,18'-bis (tripropoxysilyloctadecenyl) tetrasulfide, 4,4'-bis (trimethoxysilyl-buten-2-yl) tetrasulfide, 4,4'-bis (trimethoxysilylcyclohexylene) tetrasulfide, 5,5'-bis (dimethoxymethylsilylpentyl) trisulfide, 3,3'-bis (trimethoxysilyl-2-methylpropyl) tetrasulfide, 3,3'-bis (dimethoxyphenylsilyl-2-methylpropyl) disulfide.

The preferred sulfur containing organosilicon compounds are the 3,3'-bis(trimethoxy or triethoxy silylpropyl) sulfides. The most preferred compounds are 3,3'-bis (triethoxysilylpropyl) tetrasulfide and 3,3'-bis (triethoxysilylpropyl) disulfide. Therefore, as to Formula II, preferably Z is:

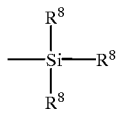

where $R^8$ is an alkoxy of 2 to 4 carbon atoms, with 2 carbon atoms being particularly preferred; Alk is a divalent hydrocarbon of 2 to 4 carbon atoms with 3 carbon atoms being particularly preferred; and n is an integer of from 3 to 5 with 4 being particularly preferred.

The amount of the sulfur containing organosilicon compound of Formula II in a rubber composition will vary depending on the level of silica that is used. Generally speaking, the amount of the compound of Formula II will range from 0 to 1.0 parts by weight per part by weight of the silica. Preferably, the amount will range from 0 to 0.4 parts by weight per part by weight of the silica.

It is readily understood by those having skill in the art that the rubber composition would be compounded by methods generally known in the rubber compounding art, such as mixing the various sulfur-vulcanizable constituent rubbers with various commonly used additive materials such as, for example, sulfur donors, curing aids, such as activators and retarders and processing additives, such as oils, resins including tackifying resins and plasticizers, fillers, pigments, fatty acid, zinc oxide, waxes, antioxidants and antiozonants and peptizing agents. As known to those skilled in the art, depending on the intended use of the sulfur vulcanizable and sulfur vulcanized material (rubbers), the additives mentioned above are selected and commonly used in conventional amounts. Typical amounts of reinforcing type carbon blacks(s), for this invention, if used, are herein set forth. Representative examples of sulfur donors include elemental sulfur (free sulfur), an amine disulfide, polymeric polysulfide and sulfur olefin adducts. Preferably, the sulfur vulcanizing agent is elemental sulfur. The sulfur vulcanizing agent may be used in an amount ranging from 0.5 to 8 phr, with a range of from 1.5 to 6 phr being preferred. Typical amounts of tackifier resins, if used, comprise about 0.5 to about 10 phr, usually about 1 to about 5 phr. Typical amounts of processing aids comprise about 1 to about 50 phr. Such processing aids can include, for example, aromatic, napthenic, and/or paraffinic processing oils. Typical amounts of antioxidants comprise about 1 to about 5 phr. Representative antioxidants may be, for example, diphenyl-p-phenylenediamine and others, such as, for example, those disclosed in the *Vanderbilt Rubber Handbook* (1978), pages 344–346. Typical amounts of antiozonants comprise about 1 to 5 phr. Typical amounts of fatty acids, if used, which can include stearic acid comprise about 0.5 to about 3 phr. Typical amounts of zinc oxide comprise about 2 to about 5 phr. Typical amounts of waxes comprise about 1 to about 5 phr. Often microcrystalline waxes are used. Typical amounts of peptizers comprise about 0.1 to about 1 phr. Typical peptizers may be, for example, pentachlorothiophenol and dibenzamidodiphenyl disulfide.

In one aspect of the present invention, the sulfur vulcanizable rubber composition is then sulfur-cured or vulcanized.

Accelerators are used to control the time and/or temperature required for vulcanization and to improve the properties of the vulcanizate. In one embodiment, a single accelerator system may be used, i.e., primary accelerator. The primary accelerator(s) may be used in total amounts ranging from about 0.5 to about 4, preferably about 0.8 to about 1.5, phr. In another embodiment, combinations of a primary and a secondary accelerator might be used with the secondary accelerator being used in smaller amounts, such as from about 0.05 to about 3 phr, in order to activate and to improve the properties of the vulcanizate. Combinations of these accelerators might be expected to produce a synergistic effect on the final properties and are somewhat better than those produced by use of either accelerator alone. In addition, delayed action accelerators may be used which are not affected by normal processing temperatures but produce a satisfactory cure at ordinary vulcanization temperatures. Vulcanization retarders might also be used. Suitable types of accelerators that may be used in the present invention are amines, disulfides, guanidines, thioureas, thiazoles, thiurams, sulfenamides, dithiocarbamates and xanthates. Preferably, the primary accelerator is a sulfenamide. If a second accelerator is used, the secondary accelerator is preferably a guanidine, dithiocarbamate or thiuram compound.

The mixing of the rubber composition can be accomplished by methods known to those having skill in the rubber mixing art. For example the ingredients are typically mixed in at least two stages, namely at least one non-productive stage followed by a productive mix stage. The final curatives including sulfur vulcanizing agents are typically mixed in the final stage which is conventionally called the "productive" mix stage in which the mixing typically occurs at a temperature, or ultimate temperature, lower than the mix temperature(s) than the preceding non-productive mix stage (s). The rubber, silica, siloxy compound of Formula I and carbon black, if used, are mixed in one or more non-productive mix stages. The terms "non-productive" and "productive" mix stages are well known to those having skill in the rubber mixing art. The sulfur vulcanizable rubber composition containing the siloxy compound of Formula I, vulcanizable rubber and generally at least part of the silica should, as well as the sulfur-containing organosilicon compound, if used, be subjected to a thermomechanical mixing step. The thermomechanical mixing step generally comprises a mechanical working in a mixer or extruder for a period of time suitable in order to produce a rubber temperature between 140° C. and 190° C. The appropriate duration of the thermomechanical working varies as a function of the operating conditions and the volume and nature of the components. For example, the thermomechanical working may be from 1 to 20 minutes.

Vulcanization of the rubber composition of the present invention is generally carried out at conventional temperatures ranging from about 100° C. to 200° C. Preferably, the vulcanization is conducted at temperatures ranging from about 110° C. to 180° C. Any of the usual vulcanization processes may be used such as heating in a press or mold, heating with superheated steam or hot air or in a salt bath.

Upon vulcanization of the sulfur vulcanized composition, the rubber composition of this invention can be used for various purposes. For example, the sulfur vulcanized rubber composition may be in the form of a tire, belt or hose. In case of a tire, it can be used for various tire components. Such tires can be built, shaped, molded and cured by various methods which are known and will be readily apparent to those having skill in such art. Preferably, the rubber composition is used in the tread of a tire. As can be appreciated, the tire may be a passenger tire, aircraft tire, truck tire and the like. Preferably, the tire is a passenger tire. The tire may also be a radial or bias, with a radial tire being preferred.

While certain representative embodiments and details have been shown for the purpose of illustrating the invention, it will be apparent to those skilled in this art that various changes and modifications may be made therein without departing from the spirit or scope of the invention.

What is claimed is:

1. A method of processing a rubber composition which comprises mixing
   (i) 100 parts by weight of at least one sulfur vulcanizable elastomer selected from conjugated diene homopolymers and copolymers and from copolymers of at least one conjugated diene and aromatic vinyl compound; with
   (ii) 0.05 to 10 phr of a compound of the formula:

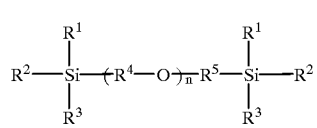

I where $R^1$, $R^2$ and $R^3$ are independently selected from alkoxy radicals having from 1 to 8 carbon atoms; $R^4$ and $R^5$ are independently selected from the group consisting of alkylenes having 1 to 12 carbon atoms, arylenes having 6 carbon atoms and alkarylenes having 7 to 10 carbon atoms and n is an integer of from 1 to 10.

2. The method of claim 1 wherein the compound of Formula I is selected from the group of formulae consisting of:

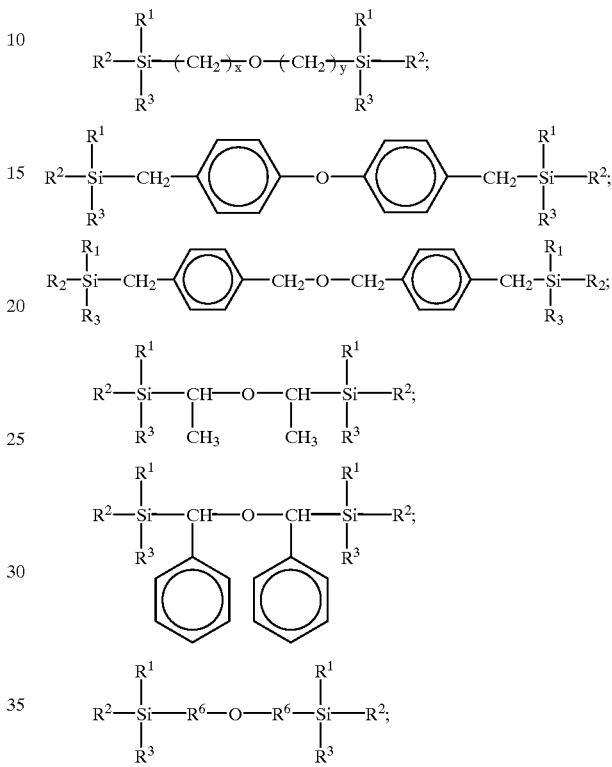

wherein x and y are individually selected from a group of integers of from 1 to 12 and $R^6$ is a cycloaliphatic group having from 5 to 8 carbon atoms in the ring.

3. The method of claim 1 wherein from 10 to 150 phr of filler is present during mixing.

4. The method of claim 3 wherein said filler is silica.

5. The method of claim 1 wherein said sulfur vulcanizable elastomer containing olefinic unsaturation is selected from the group consisting of natural rubber, neoprene, polyisoprene, butyl rubber, halobutyl rubber, polybutadiene, styrene-butadiene copolymer, styrene/isoprene/butadiene rubber, methyl methacrylate-butadiene copolymer, isoprene-styrene copolymer, methyl methacrylate-isoprene copolymer, acrylonitrile-isoprene copolymer, acrylonitrile-butadiene copolymer, EPDM, silicon-coupled star-branched polymers, tin-coupled star-branched polymers, siloxy-terminated elastomers and mixtures thereof.

6. The method of claim 1 wherein said rubber composition is thermomechanically mixed at a rubber temperature in a range of from 140° C. to 190° C. for a mixing time of from 1 to 20 minutes.

7. The method of claim 3 wherein said filler is selected from the group consisting of carbon black, aluminasilicates, clays, zeolites, modified starches and silica/carbon composites.

8. A sulfur vulcanizable rubber composition comprising an elastomer containing olefinic unsaturation and a compound of the formula:

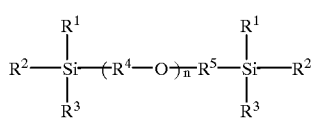                                                                 I where $R^1$, $R^2$ and $R^3$ are independently selected from alkoxy radicals having from 1 to 8 carbon atoms; $R^4$ and $R^5$ are independently selected from the group consisting of alkylenes having 1 to 12 carbon atoms, arylenes having 6 carbon atoms and alkarylenes having 7 to 10 carbon atoms and n is an integer of from 1 to 10.

9. The composition of claim 8 wherein the compound of Formula I is selected from the group consisting of:

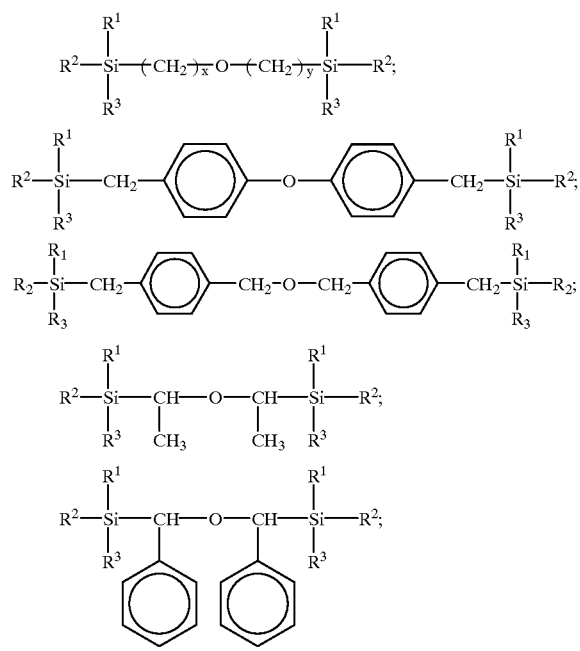

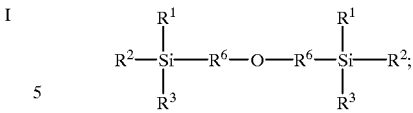

wherein x and y are individually selected from a group of integers of from 1 to 12 and $R^6$ is a cycloaliphatic group having from 5 to 8 carbon atoms in the ring.

10. The composition of claim 8 wherein from 10 to 150 phr of filler is present during mixing.

11. The composition of claim 10 wherein said filler is silica.

12. The composition of claim 8 wherein said compound of Formula I is present in an amount ranging from 1 to 5 phr.

13. The composition of claim 8 wherein said elastomer containing olefinic unsaturation is selected from the group consisting of natural rubber, neoprene, polyisoprene, butyl rubber, halobutyl rubber, polybutadiene, styrene-butadiene copolymer, styrene/isoprene/butadiene rubber, methyl methacrylate-butadiene copolymer, isoprene-styrene copolymer, methyl methacrylate-isoprene copolymer, acrylonitrile-isoprene copolymer, acrylonitrile-butadiene copolymer, EPDM, silicon-coupled star-branched polymers, tin-coupled star-branched polymers, siloxy-terminated elastomers and mixtures thereof.

14. The composition of claim 8 wherein said composition is thermomechanically mixed at a rubber temperature in a range of from 140° C. to 190° C. for a total mixing time of from 1 to 20 minutes.

15. The composition of claim 10 wherein said filler is selected from the group consisting of carbon black, aluminasilicates, clays, zeolites, modified starches and silica/carbon composites.

16. A sulfur vulcanized rubber composition which is prepared by heating the composition of claim 7 to a temperature ranging from 100° C. to 200° C. in the presence of a sulfur vulcanizing agent.

17. The sulfur vulcanized rubber composition of claim 16 in the form of a tire, belt or hose.

18. A tire having a tread comprised of the composition of claim 16.

* * * * *